(12) United States Patent
De Vos (10) Patent No.: US 10,574,180 B2
(45) Date of Patent: Feb. 25, 2020

(54) SENSOR FOR MEASURING REFLECTED LIGHT FOR OPTIMIZING DEPOSITED PERFORMANCE ENHANCEMENT COATINGS ON SUBSTRATES

(71) Applicant: Pellucere Technologies, Inc., Corvallis, OR (US)

(72) Inventor: John Arthur De Vos, Corvallis, OR (US)

(73) Assignee: Pellucere Technologies, Inc., Corvallis, OR (US)

( * ) Notice: Subject to any disclaimer, the term of this patent is extended or adjusted under 35 U.S.C. 154(b) by 0 days.

(21) Appl. No.: 15/570,829

(22) PCT Filed: May 15, 2016

(86) PCT No.: PCT/US2016/032614
§ 371 (c)(1),
(2) Date: Oct. 31, 2017

(87) PCT Pub. No.: WO2016/187082
PCT Pub. Date: Nov. 24, 2016

(65) Prior Publication Data
US 2018/0145628 A1  May 24, 2018

Related U.S. Application Data

(60) Provisional application No. 62/162,617, filed on May 15, 2015.

(51) Int. Cl.
*G01N 21/84* (2006.01)
*H02S 50/15* (2014.01)
(Continued)

(52) U.S. Cl.
CPC .............. *H02S 50/15* (2014.12); *F24S 40/00* (2018.05); *G01B 11/0625* (2013.01);
(Continued)

(58) Field of Classification Search
CPC .............. G01N 21/8422; G01N 21/88; G01N 2021/8427; G01N 2201/0221;
(Continued)

(56) References Cited

U.S. PATENT DOCUMENTS

| | | | |
|---|---|---|---|
| 6,624,884 B1 * | 9/2003 | Imaino | G01N 21/88 356/237.2 |
| 2010/0032573 A1 * | 2/2010 | Shelley | G01B 11/0625 250/341.8 |

(Continued)

*Primary Examiner* — Hina F Ayub
*Assistant Examiner* — Amanda Merlino
(74) *Attorney, Agent, or Firm* — Chernoff, Vilhauer, McClung & Stenzel LLP (57) ABSTRACT

An innovative portable reflected light sensor for non-destructively measuring characteristics of performance enhancement coatings applied to substrates such as solar photovoltaic panels is described. The innovative portable sensor provides a light source and a photodetector for measuring light incident on a substrate surface from the light source, and reflected to the photodetector. The spot size of the illuminated region of the substrate is at least 1 cm² in area, thus averaging over a relatively wide portion of the substrate surface relative to existing fiber optic devices. A single measurement may then be representative of the coating. The innovative portable reflected light sensor is adapted to measure substrates in the field, and is especially adapted for assessing coating quality during the coating process. The innovative sensor also comprises a signal processing circuit that performs analysis of the measurements and feeds back status of the coating to the operator for coating process control.

27 Claims, 6 Drawing Sheets

(51) Int. Cl.
*G01B 11/30* (2006.01)
*G01B 11/06* (2006.01)
*H02S 50/10* (2014.01)
*F24S 40/00* (2018.01)

(52) U.S. Cl.
CPC ......... *G01B 11/30* (2013.01); *G01N 21/8422* (2013.01); *H02S 50/10* (2014.12); *G01N 2021/8427* (2013.01); *G01N 2201/0221* (2013.01); *Y02E 10/40* (2013.01)

(58) Field of Classification Search
CPC ..... G01B 11/06; G01B 11/30; G01B 11/0625; H02S 50/15; H02S 50/10
See application file for complete search history.

(56) References Cited

U.S. PATENT DOCUMENTS

| | | | | |
|---|---|---|---|---|
| 2010/0053599 A1* | 3/2010 | Milster | ...................... | G01J 3/02 |
| | | | | 356/51 |
| 2015/0015959 A1* | 1/2015 | Lee | .......................... | G02B 1/11 |
| | | | | 359/586 |
| 2017/0008022 A1* | 1/2017 | deVos | ...................... | C08K 3/36 |

* cited by examiner

Fig. 5

SENSOR FOR MEASURING REFLECTED LIGHT FOR OPTIMIZING DEPOSITED PERFORMANCE ENHANCEMENT COATINGS ON SUBSTRATES

CROSS REFERENCE TO RELATED APPLICATIONS

This application is a continuation of International Application No. PCT/US2016/032614, filed May 15, 2016, which claims the benefit of U.S. Provisional Application No. 62/162,617 filed on May 15, 2015.

FIELD OF THE INNOVATION

This invention relates to portable light reflectance sensors that measure surface or thin film characteristics for large substrates, such as solar photovoltaic panels.

BACKGROUND

Currently available light reflection sensors are not capable of measuring the light reflection from a relatively large spot size on the top surface of solar panels installed in the field and comparing the results before and after application of a performance enhancement coating. The very small spot size analyzed by a typical sensor using a fiber optic probe is insufficient to accurately measure in one reading an area large enough to determine the average performance across the whole solar panel of solution deposited performance enhancing coatings. This is due in part because variations in the top surface structure of solar panel cover glass and variations in solution deposited coating may not be adequately represented within the very small spot size read by the fiber optic probe. Multiple readings by such a probe would have to be done to develop a statistically significant number of samples to estimate average coating performance. Furthermore, typical fiber optic probe sensors require the use of a separate computing device, such as a laptop computer, to run the calculations required to produce human readable data. The process of taking numerous measurements and transporting and setting up a typical fiber optic sensor with a separate computing device for each solar panel to be measured is relatively cumbersome and time consuming compared with a device with integrated computing and human readable display that can determine the average performance difference in light reflection properties by taking just one measurement before and just one measurement after application of a performance enhancement coating.

BRIEF SUMMARY OF THE PRESENT INVENTION

The instant innovation relates to application of liquid performance enhancing coating precursor solution to large substrates such as photovoltaic panels. The instant innovation is a portable light reflectance sensor for non-destructively determining characteristics of thin film performance enhancing coatings applied to a substrate, such as, but not limited to, a photovoltaic panel. It is particularly advantageous for outdoor installations, where photovoltaic panels installed in arrays or individually may be retrofitted with performance enhancement coatings, such as, but not limited to, anti-reflection coatings. The innovative portable light reflectance sensor provides a light source and a photodetector for measuring light incident on a substrate surface from the light source, and reflected to the photodetector. The spot size of the illuminated region of the substrate is at least 1-centimeter square in area, thus averaging over a relatively wide portion of the substrate surface vs. the much smaller spot size of a fiber optic measuring device. A single measurement may then be representative of the coating. The innovative light reflectance sensor is adapted to measure substrates in the field, and is especially adapted for assessing coating quality during the coating process. The innovative portable sensor also comprises a signal processing circuit that performs analysis of the measurements and feeds back status of the coating to the operator for coating process control.

The coating of such panels may be facilitated by a mobile coating apparatus, such as detailed in co-pending U.S. patent application Ser. No. 14/668,956 incorporated herein in its entirety. The innovative detector comprises a light source adapted to illuminate a region of a substrate with a spot cross-sectional area of at least 1 $cm^2$ at the substrate surface, and a photodetector adapted to collect at least a portion of the light reflected from the substrate surface. In one embodiment, the innovative photodetector further comprises signal processing circuitry adapted to digitize the raw analog data collected by the photodetector. The photodetector may comprise a spectrometer that resolves the intensity of reflected light as a function of wavelength. In other embodiments, the photodetector comprises a photodiode or phototransistor. Both types may integrate the total light intensity over the entire capture spectrum of the reflected light. A variation includes the use of a bandpass filter or cutoff filters to examine a portion of the visible or invisible spectrum, the latter referring to the infrared (IR) and the ultraviolet (UV) extensions of the visible spectrum. In other embodiments, sources having a narrower range of wavelengths, such as lasers, light emitting diodes (LEDs), cold cathode and heated cathode gas discharge lamps, such as mercury lamps and inert gas plasmas, may be employed as light sources.

The relatively large spot size of the incident beam provides the advantage of spatially integrating surface features over the area covered by the illuminated region covered by the spot. In this way, the innovative reflectance sensor is further adapted to spatially and temporally integrate the spectral characteristics of the light reflected and collected from the illuminated region of the substrate, where the photodetector is in electronic communication with the signal processing circuit. The signal processing circuit may be adapted to perform read operations to capture the signals from the photodetector on receiving a command signal, and may be further adapted to extract and store digitized photometric data from the captured sensor signal. In addition, the signal processing circuit may be adapted to perform computations on the photometric data, and then correlate the data to the one or more of the characteristics of the thin film coating on the substrate of interest. It is an aspect of one embodiment of the instant innovation that the correlated characteristics of the coating be transformed into control information to be fed back to either a human operator or to a controlling device for assessing the quality of the coating as it is applied from a liquid coating precursor solution, and if necessary adjusting the coating deposition method, or coating make-up characteristics. In this way, the deposition process may be steered to produce a finished coating having optimal performance.

A coating apparatus adapted to apply a film of liquid precursor solution that cures into a finished performance enhancement coating, such as, but not limited to, an anti-reflection coating, may be used in conjunction with the innovative portable reflectance sensor to provide a feedback component in the control loop of the coating process. The coating apparatus may be controlled manually by a human operator, or automatically or semi-automatically by an automated control system. In the automatic or semi-automatic cases, the innovative portable sensor may be used as a feedback component in a closed control loop.

It is an aspect of the innovation that the light source produces a light beam having a spot cross-sectional area of at least 1 $cm^2$ at the substrate surface. Commercially available light sensors based on total reflection and/or spectral reflection measurements used for measuring thin film or substrate surface characteristics use small spot sizes (typically 1-2 mm in diameter). Many of these devices are designed for use in measuring surface characteristics of small substrates, such as silicon wafers. For both large and small substrates, multiple readings taken at several locations on the substrate are generally necessary to obtain a representative sample of coating or surface characteristics. The larger spot size of the instant invention allows integration of superficial properties over an area 50-100 times or larger than that provided by conventional fiber optic devices, providing a representative sampling of the local region of the surface from which the light is reflected.

It is another aspect of the invention to provide a means to correlate photometric data obtained from the light reflected off of a substrate surface and collected by the photodetector. For example, the surface may have a previously-cured performance enhancement coating, such as an anti-reflection coating, or a freshly applied liquid coating precursor solution. Optionally, the surface may be uncoated, where a measurement may be made to obtain baseline data of initial reflectance for a before-and-after comparison when a coating is applied. The raw photometric data collected may provide a measure of the reflectance of the substrate surface, as, for example, to measure the attenuation of percent reflection after application of an antireflection coating.

Another measurement derived from the raw photometric data may be the thickness and quality of coverage of a fresh layer of coating precursor solution. The photometric data may be in the form of spectral intensity data. In this case, the photodetector may incorporate a spectrometer that can scan over a range of wavelengths. In other embodiments, the photodetector may be a simple photodiode or phototransistor that is adapted to measure across a broad spectrum of light, and may be used to measure intensity integrated over the entire visible, near IR and UV spectrum to which is it sensitive, or a portion thereof, if, as an example, a bandpass filter is used. It is another aspect of the instant innovation that this information may be used for feedback control in a coating process control loop for the coating apparatus. The coating apparatus may be controlled by a human operator in one set of embodiments, thus the control loop is an open loop, or may be machine-controlled in another set of embodiments, necessitating a closed feedback control loop.

The signals may be used to indicate the thickness of a coating. As an example, a relatively high average reflectance intensity reading and a shift toward the reddish part of the spectrum in the reflected light may indicate that a performance enhancement coating is too thick as applied. The operator or automatic control system may need to adjust the speed of the applicator, or decrease coating precursor solution viscosity. As the spot size is large, variations normally encountered in both coating non-uniformities and variations in the underlying substrate surface, such as photovoltaic panel cover glass or photovoltaic cell surface, are integrated over the spot area and collected by the photodetector. Thus, the photodetector receives a reflection spectrum that is averaged over the relatively large spot size. The spectral intensity data may be averaged over a range of wavelengths to determine a predominant component or spectral region. By subtracting the reading from one area measured prior to coating from the reading of the same area after coating, variations other than those of the coating itself may be canceled out.

Multiple readings may be made, for example, over very large areas where several locations on the substrate surface or multiple substrate surfaces may be sampled. In this way, the uniformity of surface characteristics may be assessed. As an example, for an anti-reflection coating, the uniformity of the coating thickness and quality may be quantified. This is particularly advantageous for applying new coatings to a substrate such as a photovoltaic panel or to multiple substrates such as a solar panel array. An operator of a coating apparatus may use the innovative portable reflectance sensor to monitor the quality of the coating process by measuring the spectral characteristics of the reflected light. As an example of a method of use, an operator of the coating apparatus may first take baseline measurements on an uncoated photovoltaic panel, then apply a thin film of liquid precursor solution that will cure to form a finished coating, such as an antireflection coating.

The innovative portable reflectance sensor may include signal processing circuitry comprising an on-board microprocessor and memory, on which may be stored one or more algorithms and/or look-up tables for correlation of measurements to known film characteristics. As an example, the portable sensor may include a spectrometer that is programmed to scan a range of wavelengths and record spectral intensities. The data may be digitized and stored as binary data in the on-board memory, where the microprocessor may compare the intensity data reflected from the freshly applied liquid coating to the baseline data taken from the bare (uncoated) surface of the photovoltaic panel. In another embodiment, the data may also be offloaded to an off-board data storage and retrieval system, accessed by the portable sensor using wired or wireless means.

As an example of process control by use of the innovative portable sensor, the comparison algorithm may reveal that the reflection spectral intensities are higher than expected for an antireflection coating, and moreover the intensities are stronger in the red end of the spectrum measured, having been red-shifted in comparison to the expected spectrum reflected (for example in comparison with a ¼ wave-thick index matching film). These spectral characteristics would indicate that the coating is too thick. In this example, it may be thicker than the ¼ wavelength thickness necessary to cancel reflections at more centralized wavelengths, thus being detuned and allowing longer wavelengths to be reflected than would be the case for a film with the proper ¼ wavelength thickness.

A further aspect of the innovation may be the inclusion of an algorithm to present recommendations to the operator as to steps required to adjust the coating process to optimize the coating. Here, the coating thickness may be a function of applicator speed and viscosity of the liquid coating precursor solution. The coating process may be adjusted, for example, by changing applicator speed, or by changing solution viscosity. In addition, the coating thickness may be corrected, if found to be out of specification by measurements taken with the innovative portable sensor, by applying a make-up coating.

In further embodiments of the innovation, measurements of air temperature and surface temperatures of the substrate may be incorporated into the portable sensor system design and algorithms. Thermal measurements may be used for further optimization of the coating process, as evaporation rates and curing rates may be taken into consideration by the optimization algorithm, preferably stored in on-board memory and executed by an on-board microprocessor, thereby adjusting the recommendations to the operator as to the optimal coating speed and solution viscosity, for example. In further embodiments, humidity sensors may also be a part of the sensor array to further refine the coating process, if, as an example, relative humidity affects the evaporation rate of the solvent used in the precursor solution, or if humidity affects (or is necessary to initiate) the curing chemistry of the coating.

In other embodiments of the instant innovation, an automated control system may replace the operator of the coating apparatus as being the recipient of the feedback from the innovative portable sensor signal processing circuitry. The automated control system may be adapted to directly respond to the feedback issuing from the innovative portable sensor signal processing circuitry. In one example, the innovative portable sensor may be mounted on a coating apparatus, and configured to continuously or intermittently measure the surface characteristics by reflection spectrometry. In this example, the portable sensor is aimed at the substrate surface behind the apparatus, so that the freshly coated surface may be measured. The characteristics of the freshly applied coating may be assessed, and the speed of the coating apparatus may be controlled by a closed feedback loop. In other embodiments, one portable sensor may be situated in such a way as to measure the substrate reflection before coating and another portable sensor may be situated to measure the substrate reflection after coating, with the difference in reflection measurements being used to inform the coating process.

DETAILED DESCRIPTION OF THE PRESENT INVENTION

Figure 1A:
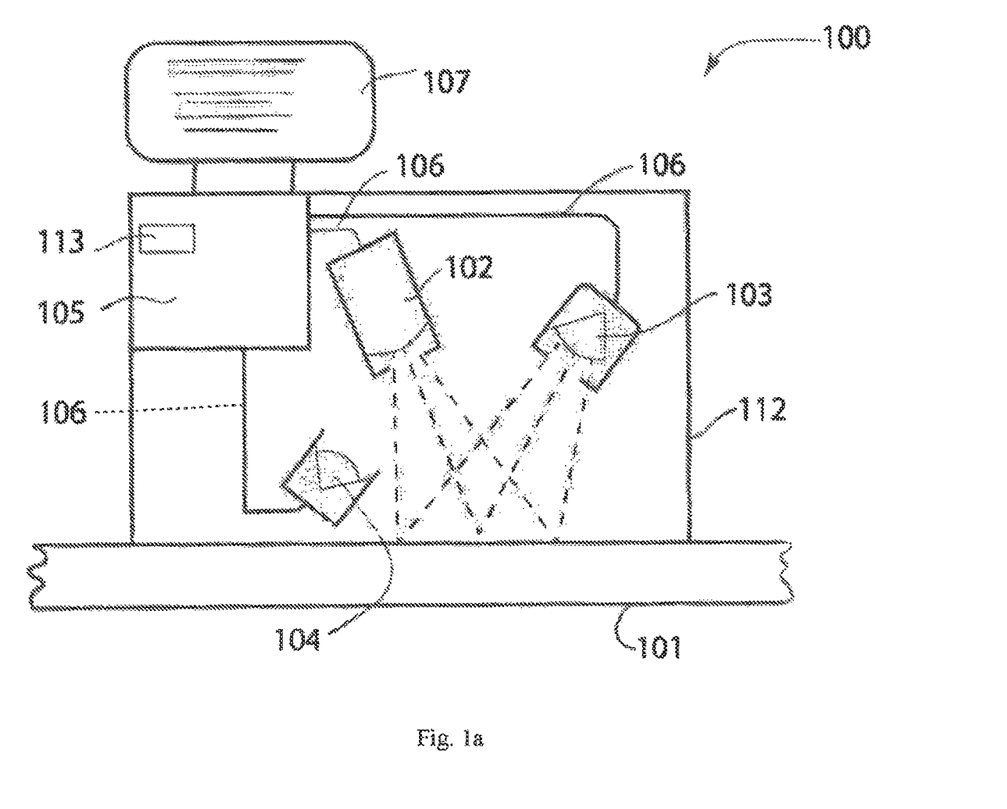
FIG. 1a. Schematic representation of the componentry of the innovative portable sensor, showing an embodiment comprising a photodetector.

FIG. 1a details a schematic of the instant innovation as described. Portable sensor system (100) is shown in active deployment as a portable device, where it is disposed on a substrate surface, where substrate (101) is undergoing measurement. Incident light source (102) shines light, which may be substantially broadband light ('white' light) or narrow banded colored light, emanating from a variety of light sources. For instance, incandescent light sources may be used having coatings yielding different IR and visible spectra, or black body temperatures, as is commercially available with incandescent bulbs. Other sources may be used as well, such as mercury lamps, inert gas glow discharge (cold and heated cathode) sources, LED or laser sources. In addition, 'white' light sources using bandpass or cutoff filters may be employed. The choice may be dictated by the desired spectral range of the incident light. Light rays are shown incident on substrate (101), and reflected specularly to photodetector (103).

Additional embodiments of this innovation may include multiple light sources of the same or different types and multiple photodetectors of the same or different types. The different types may be used to detect more accurately particular wavelengths of interest. For example, a light source and/or photodetector tuned to more accurately identify blue wavelengths in conjunction with a light source and/or photodetector tuned to more accurately identify green and or red wavelengths may provide accurate information about the characteristics of the coating without having to integrate over the whole spectrum. Such specially tuned light sources and/or photodetectors may operate in parallel or sequentially to each other in the measurement process.

This is shown in FIG. 1a, where secondary photodetector (104) is positioned to gather peripheral light emanating from source (102). Signals from photodetectors (103) and (104) are routed to signal processing board (105) via cables (106). Board (105) is also in electronic or electrical communication with light source (102) via a cable (106). In addition, board (105) is in electronic communication with display (107). An additional output port (113) is shown on board (105) where output port may be a USB port, RS232 port or a parallel port for data exchange with an external computing device. In other embodiments, a wireless communication IC, such as a Bluetooth, cellular or WIFI IC may also be included for wireless communication with an external computing device or the internet.

Figure 1B:
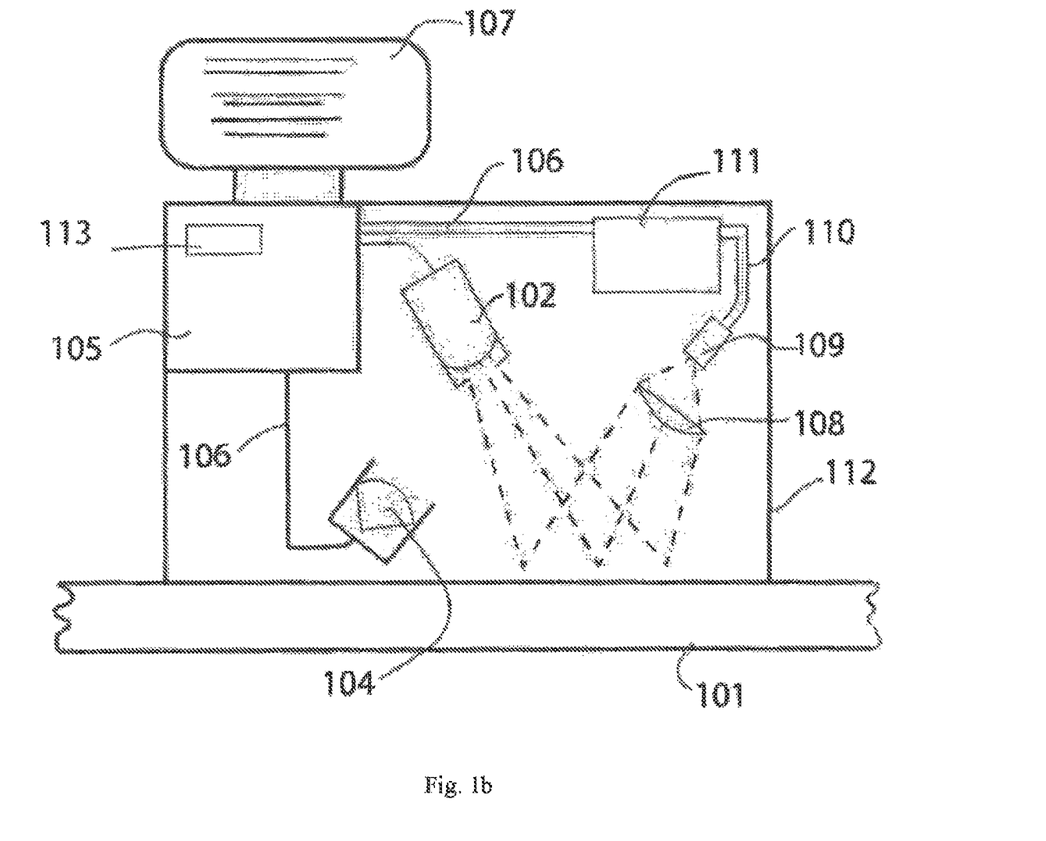
FIG. 1b. Schematic representation of the componentry of the innovative portable sensor, showing an embodiment comprising a spectrometer.

In other embodiment of this innovation, one or more secondary photodetectors (104) may be used in conjunction with the primary photodetector to measure and monitor the light output from the one or more light sources themselves, and feed data back to the microprocessor in order to correct for light source fluctuations or light source drift that can change the reflection measurements. FIG. 1b, photodetector (103) is replaced by lens (108). Lens (108) gathers reflected light and focuses it to the entrance of an optical fiber coupler (109). Light is then guided via optical fiber (110) to spectrometer or spectrophotometer (111), which is shown to be tied to board (105) via cable (106). Board (105) may comprise a microprocessor that reads spectral data from spectrometer (111) on command. Other embodiments of the instant innovation may comprise a combination of spectrometer (111) and photodetector (103). An example of a suitable miniature spectrometer to fulfill this role is an Avantes AvaSpec Micro, the STS Microspectrometer from Ocean Optics, to name a few of a number of suitable devices.

Figures 2A, 2B:
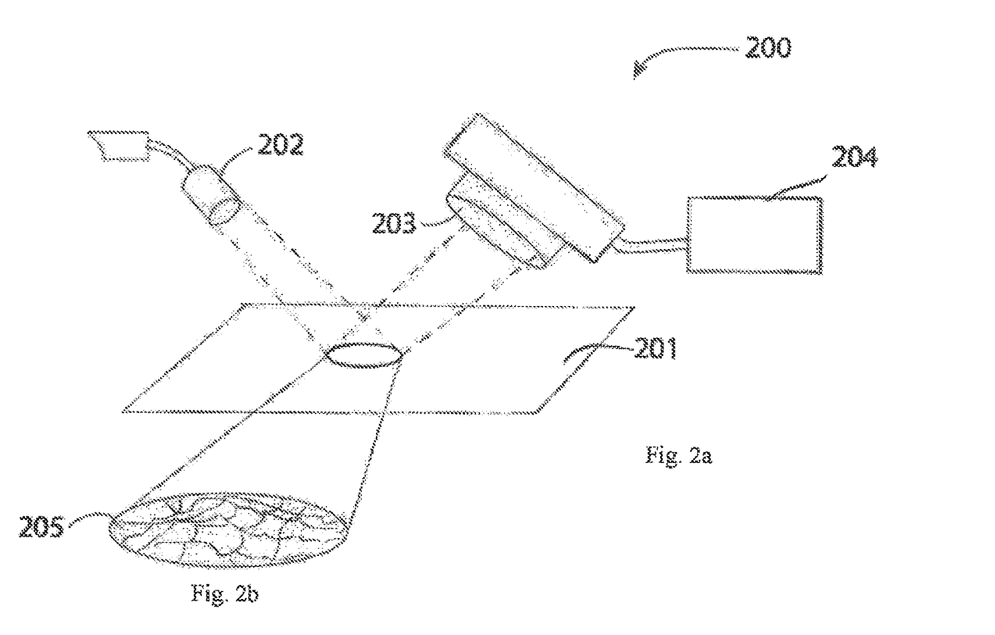
FIG. 2a. Operational schematic of the innovative portable sensor.
FIG. 2b. Zoom view of an illuminated portion of a substrate surface (coated or uncoated), showing surface irregularities and non-uniformities FIG. 3. Mobile coating apparatus example deployed on a photovoltaic panel, where the innovative portable sensor is mounted on the chassis of the apparatus.

In FIG. 2a, the basic schema of the innovative portable sensor is again shown, with substrate (201) illuminated by light source (202), and reflecting light to photodetector (203) which feeds its signal to signal processing board (204). According to the innovation, the spot size cross-sectional area is at least 1 $cm^2$ in area. In FIG. 2b, a zoom view of the region illuminated by the incident light is shown. The illuminated region has a plurality of non-uniformities in a portion of coated substrate, where a plurality of small asperities and thin areas are present, resulting in micro-variations of coating thickness. In this embodiment, photodetector (203) is not adapted to spatially resolve the light impinging upon it. Individual light rays reflected from the totality of these micro-variations may be integrated when collected at the photodetector (203) such that the intensity variations in the individual light rays are spatially averaged as to a single signal level. Photodetector (203) may comprise a spectrometer, adapted to resolve light intensity as a function of wavelength. Alternatively, photodetector may comprise a photodiode or phototransistor adapted to yield a voltage level corresponding to the averaged light intensity of the reflected light. Filters, such as bandpass or cutoff filters, may furthermore be used to block portions of the light spectrum in conjunction with a photodiode or phototransistor detectors to approximate a spectrometer.

Figure 3:
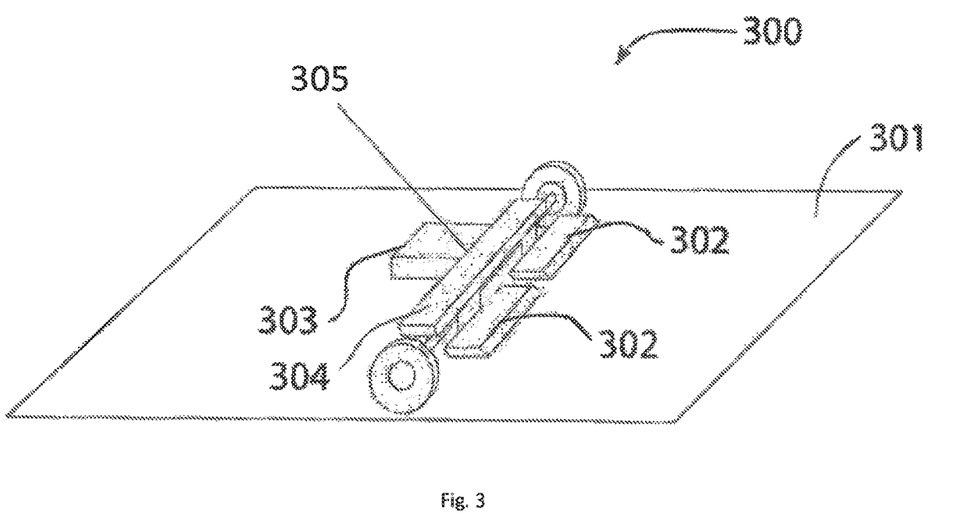

Referring again to FIG. 2a, the signal generated by photodetector (203) is fed to signal processing circuit (204) which is in electronic communication with photodetector (203). In FIG. 3 a coating apparatus (300) of the type described in co-pending U.S. patent application Ser. No. 14/668,956 incorporated herein in its entirety, is shown moving along substrate (301). The speed and trajectory of coating apparatus (300) may be fully manually controlled by a human operator, or fully automatically controlled, or may be at least partially controlled automatically, with some degree of guidance or handling by a human operator. Coating apparatus (300) comprises coating heads (302) and a mounted embodiment of the instant innovation (303). An arrow shows the direction of travel by apparatus (300). The instant innovation (portable sensor) (303) is shown mounted on the chassis (304) of coating apparatus (300) where it extends over aft or rear portion.

Figure 4:
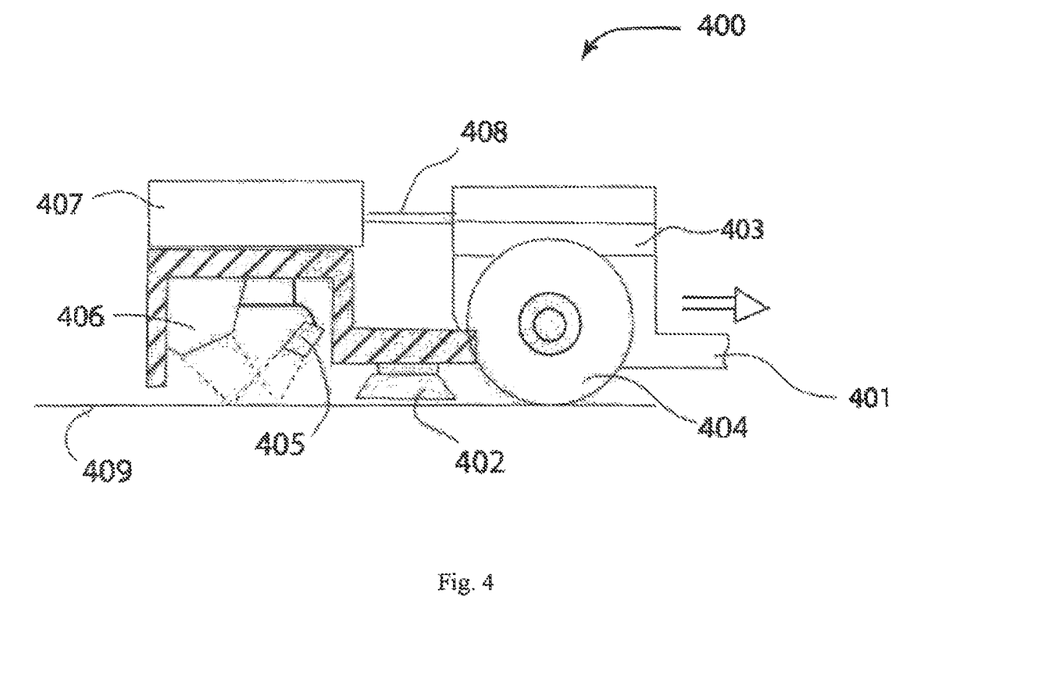
FIG. 4. A side-sectional view of an embodiment of the innovative portable sensor mounted on a coating apparatus.

In FIG. 4 a detailed side sectional view of the innovative portable sensor (400) based on the mounted embodiment (203) of FIG. 2). Portable sensor (300) as described in the instant disclosure is shown mounted on the rear side of chassis (401) of the mobile coating apparatus. Also shown affixed to chassis (401) is coating head (402) and motor (403) that is coupled to wheel (404). Portable sensor (400) is shown as a side sectional view, revealing internal components. These components comprise light source (405) and photodetector (406) where source (405) shines a wide beam of light making a spot size with a cross-sectional area of at least 1 cm$^2$ on the surface of substrate (409). Light is reflected from substrate (409) to photodetector (406).

As specified above, photodetector (406) may be a spectrometer adapted to scan over a range of wavelengths, or a photodiode or phototransistor that integrates light intensities over a large range of wavelengths. As described above, the raw signal from photodetector (406) is fed to signal processing board (407) comprising a microprocessor and an on-board memory. The microprocessor may execute algorithms stored in on-board memory that digitize the analog signal to binary data, then analyze the data as photometric measurements such as spectral data, or overall reflectance data to show changes in surface reflectance before and after application of a coating solution by the coating apparatus. The analysis routines may require baseline data for comparison, thus requiring a measurement of the uncoated substrate or of a previously coated substrate. Before-and-after data may be compared, and changes in the spectral characteristics or reflectance values may be correlated to coating characteristics, such as film thickness.

For this conclusion, a look-up table may be employed by the microprocessor, or calculation formulas may be employed as part of the algorithm. As an example, a red shift in the reflectance spectrum may indicate that the film is too thick. The algorithms may then generate feedback control data that may be output as human-readable values, or as command signals to motor drive electronics, forming a closed control loop with the motor drive. Referring to FIG. 4 signal processing board (407) is shown in electronic communication with drive electronics of motor (403) via signal cable (408). The command signals may command the motor to slow down, since the film thickness decreases at slower speeds of the mobile coating apparatus.

Figure 5:
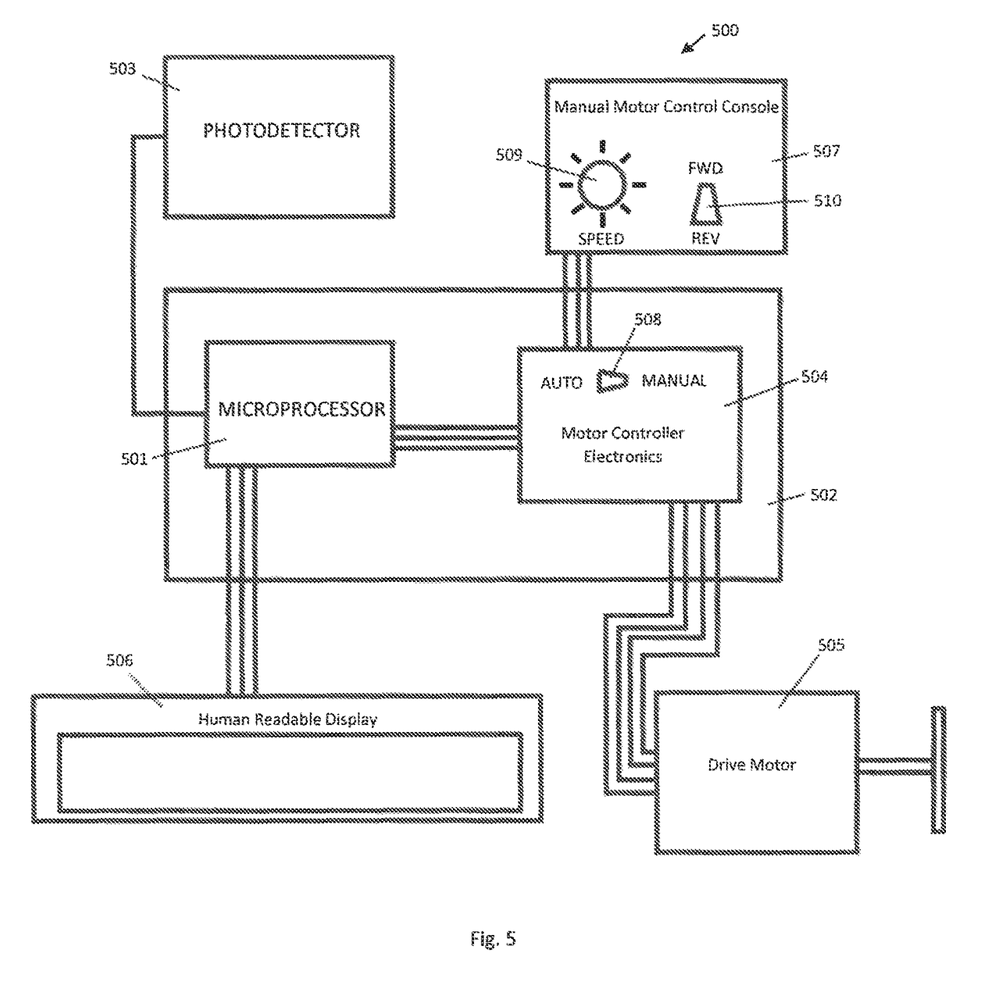
FIG. 5. Schematic diagram of an electronic control system embodiment for controlling a mobile coating apparatus.

An embodiment of the above description is shown more explicitly in the diagram of FIG. 5 showing a control system (500) for a mobile coating apparatus, for example, as described in co-pending U.S. patent application Ser. No. 14/668,956) the contents of which are incorporated herein in their entirety. The exemplary mobile coating apparatus control system (500) may be governed partially or fully by microprocessor (501) which may be physically incorporated on signal processing board (502).

Microprocessor (501) is shown to be in electronic communication with both photodetector/spectrometer (503) and motor controller electronics board (504). Analog voltage or current signals issuing from photodetector/spectrometer (503) may be digitized to binary code by an analog to digital converter (ADC) unit residing on photodetector (503) itself, or by an ADC integrated on the microprocessor chip, or by a separate ADC unit residing on signal processing board (502). Raw analog signals generated by photodetector/spectrometer (503) may constitute photometric data, wherein the photometric data may comprise spectral information, or at least integrated light intensity information. The photometric data in turn relate characteristics of the coating, in the uncured or cured state, such as total reflectance, spectral reflectance, and indirect measurements such as film thickness and roughness. Conversion of photodetector signals into binary format may constitute photometric data, read by microprocessor (501).

Consequently, microprocessor (501) may issue motor control commands generated by one or more algorithms embodied in software stored in a RAM or ROM accessible by microprocessor (501) where the algorithms process the output of photometric data from photodetector/spectrometer (503). Commands issued by microprocessor (501) may be received by motor control electronics board (504) in the form of continuous analog voltage levels or voltage pulses to drive a stepper motor or a dc motor, either type shown schematically by motor (505). Both motor direction and speed may be controlled by motor control electronics board (504). The control circuitry constitutes a closed-loop embodiment of the mobile coating apparatus control system, which is automatic control based on decisions made by algorithms embodied in the software executed by microprocessor (501).

In another embodiment, the mobile coating apparatus control system may be an open-loop control system. Microprocessor (501) is also shown to be in electronic communication with human-readable display (506) whereas motor control electronics board (502) is shown also to be in electronic communication with manual motor control console (507). In the open-loop control scheme, a human operator may read output displayed on human-readable display (506) which may be a serial or parallel input LCD display. In the example shown in FIG. 5 a selection switch (508) is provided to select between manual control or microprocessor control of the motor controller electronics. To facilitate manual coating process control, the analysis algorithms embodied by software stored on a RAM or ROM accessible to microprocessor (501) may be adapted to communicate process optimization recommendations that are electronically displayed to the human operator, using human-readable display (506) disposed on a hand-held or apparatus—mounted innovative portable sensor, as an example. Microprocessor (501) may also be in electronic communication with a wireless network interface (not shown) adapted to transmit data over the internet wirelessly in some embodiments for display on a computing device.

Characters output from microprocessor (501) to human-readable display (506) may be in a format understandable to the human operator, and indicate, for example, recommendations of motor speed and/or direction may be controllable by the human operator, in order to maintain optimized coating quality. The decision as to what speed the apparatus should be travelling along the substrate, for example, may be based on photometric data generated by photodetector/spectrometer (503). By way of example, the photometric data may indicate coating thickness, which may be dependent on the speed of the apparatus. These recommendations may also include exhortations to decrease the viscosity of the coating solution, and or change the make-up coating to optimize coating performance. In the open-loop control embodiment, control data are output to the human operator by means of human-readable display (506). The human operator may read and interpret the control data, and control the speed and direction of motor (505) by means of manual motor control console (507). Rotary manual speed control (509) may comprise a potentiometer or a rotary encoder. Other forms of manual control may be used, such as a linear slider potentiometer. Double throw switch (510) may be manipulated to control motor direction, causing the mobile coating apparatus to advance in the forward direction or reverse.

Example of Method of Use

An example of how the instant innovation is employed will now be described. A substrate such as a photovoltaic panel may be deployed in an array or individually in an outdoor setting. It is desired to retrofit the panel with an anti-reflective coating, for which a coating apparatus of the type disclosed in co-pending U.S. Non-provisional patent application Ser. No. 14/668,956 is provided. This coating device may comprise wheels and coating heads such that it may be deployed to roll over a photovoltaic panel and deposit a liquid coating pre-cursor solution that is to be cured after application.

An operator equipped with a portable version of the innovative portable light reflectance sensor may deploy it on the panel surface before the coating is applied, to obtain a baseline measurement of percent reflection of incident light as the photometric data. After the baseline measurement, the coating is applied by the coating apparatus. A second percent reflection measurement is then taken. Data from both measurements are digitized by the signal processing circuit and stored in an on-board memory.

The data are then processed by the signal processing circuitry on-board the instant portable sensor, as described above, where the two measurements are compared. A change in percent reflection obtained, with data from the second measurement correlated to the state of the newly applied coating solution. The signal processing circuit then displays the information to the operator. If the coating is too thick or thin, instructions or recommendations are displayed to the operator as a method of feeding back to the operator in control to adjust the speed of the coating apparatus, or to alter the viscosity of the coating solution. The information may also be conveyed by connection to a laptop computer, or wirelessly to a smart phone in possession of the operator at the site, or to personnel at a remote site.

The embodiments of the innovation disclosed and described above are exemplary, and by no means are meant to be construed as limiting the innovation. It is recognized by persons skilled in the art that other variations are possible without departing from the scope and spirit of the innovation, as claimed in the claims below.

What is claimed is:

1. An apparatus comprising:
A. one or more portable sensors for determining characteristics of performance enhancement coatings applied to the surface of one or more solar panels in an outdoor solar panel array by one or more performance enhancement coating heads, the one or more portable sensors comprising:
   i. one or more light sources adapted to illuminate a region of a solar panel surface with a spot cross-sectional area of at least 1 cm$^2$, at the surface of the one or more solar panels;
   ii. one or more photodetectors adapted to collect at least a portion of the light emanating from said one or more light sources that is reflected from said solar panel surface, said one or more photodetectors adapted to output an electronic signal proportional to one or more characteristics of the reflected light; and
   iii. a signal processing circuit in electronic communication with the one or more photodetectors, wherein said processing circuit is adapted to read and process the electronic signal output by the one or more photodetectors, the signal processing circuit being part of a feedback loop for controlling the coating speed of the one or more performance enhancement coating heads;
   iv. one or more photodetectors to monitor the one or more light sources to detect if the one or more light sources drift;
B. one or more performance enhancement coating heads for depositing one or more layers of performance enhancement coating solution on to the one or more solar panels;
C. a mechanism to move the coating heads across the one or more solar panels by way of rolling motion, wherein the mechanism comprises wheels;
wherein the one or more portable sensors are used to determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from a first coated area of the one or more solar panels equal to or greater than 1 cm$^2$ comprising non-uniformities in the at least one or more solar panels' cover glass, non-uniformities in a photovoltaic cell surface, and non-uniformities in the coating on the one or more solar panels;
wherein the one or more portable sensors are used to determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from a second coated area of the one or more solar panels equal to or greater than 1 cm$^2$ comprising non-uniformities in the at least one or more solar panels' cover glass, non-uniformities in a photovoltaic cell surface, and non-uniformities in the coating on the one or more solar panels;

wherein the signal processing circuit determines if the coating is too thick by determining if the light received from the second coated area of the one or more solar panels is shifted toward the reddish end of the light spectrum relative to the light received from the first coated area of the one or more solar panels by comparing the light reflection intensity in at least part of the red or infrared range of the light spectrum or the light reflection intensity in at least part of the ultraviolet range from the second coated area with the light reflection intensity in at least part of the red or infrared range of the light spectrum or the light reflection intensity in at least part of the ultraviolet range from the first coated area or comparing the light reflection intensity across the spectrum from both the first coated area and the second coated area to the expected spectrum reflection such as the reflected spectrum from a ¼ wave-thick index matching film; and wherein the signal processing circuit triggers a reduction in the speed of the rolling movement that moves the coating heads across the solar panel if the light received from the second coated area of the solar panel is shifted toward the reddish end of the light spectrum relative to the light received from the first coated area of the solar panel.

2. The apparatus of claim 1, wherein the signal processing circuit is further adapted to extract photometric data from said electronic signal output by the photodetector and correlate the photometric data to one or more characteristics of the performance-enhancement coating deposited by the mobile coating apparatus on said solar panel surface.

3. The apparatus of claim 2, wherein the photometric data are measurement data of reflection intensity from the solar panel surface.

4. The apparatus of claim 2, wherein the photometric data are an array of measurement data of spectral intensity over a wavelength range from the solar panel surface.

5. The apparatus of claim 2, wherein the photometric data are measurement data of percent reflection from the solar panel surface.

6. The apparatus of claim 2, wherein the photometric data are measurement data of averaged spectral intensity over a wavelength range from the solar panel surface.

7. The apparatus of claim 2, wherein the signal processing circuit is further adapted to compare photometric data captured from the photodetector on successive read operations.

8. The apparatus of claim 2, wherein the signal processing circuit is further adapted to correlate the data extracted from the photodetector signal to one or more characteristics of a performance enhancement coating.

9. The apparatus of claim 8, wherein the signal processing circuit is further adapted to output at least one of the one or more correlated characteristics of a performance enhancement coating in a human-readable format.

10. The apparatus of claim 9, wherein the signal processing circuit outputs the at least one of the one or more correlated characteristics of the performance enhancement coating in a human-readable format to a human-readable display.

11. The apparatus of claim 8, wherein the signal processing circuit outputs the at least one of the one or more correlated characteristics of the performance enhancement coating to an external computing device.

12. The apparatus of claim 11, wherein the external computing device is accessed wirelessly.

13. The apparatus of claim 8, wherein the signal processing circuit outputs the at least one of the one or more correlated characteristics of the performance enhancement coating to an external storage device.

14. The apparatus of claim 13, wherein the external storage device is accessed wirelessly.

15. The apparatus of claim 1, wherein the performance enhancement coating is an energy enhancement film.

16. The apparatus of claim 15, wherein the energy enhancement film is an antireflection coating.

17. A sensor-based feedback controlled solar panel coating system, comprising:

A. a mobile coating apparatus having a means for applying one or more layers of performance enhancement coating solution to one or more solar panels in an outdoor solar panel array; wherein, the means for applying the one or more layers of performance enhancement coating solution comprises one or more performance enhancement coating heads that are moved across the one or more solar panels by rolling motion;

B. one or more portable sensors, comprising:
  i. one or more light sources adapted to illuminate the surface of the one or more solar panel surface with a spot size of at least 1 $cm^2$ at the surface of the one or more solar panels;
  ii. one or more photodetectors adapted to collect at least a portion of the light emanating from said one or more light sources that is reflected from said surface of the one or more solar panels; and
  iii. a signal processing circuit in communication with the one or more photodetectors, wherein said processing circuit is adapted to perform read operations to capture the signals read from the one or more photodetectors, the signal processing circuit being part of a feedback loop for controlling the coating speed of the mobile coating apparatus for depositing the performance enhancement coating solution;

wherein the one or more portable sensors are used to determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from a first coated area of the one or more solar panels equal to or greater than 1 $cm^2$ comprising non-uniformities in the at least one or more solar panels' cover glass, non-uniformities in a photovoltaic cell surface, and non-uniformities in the coating on the one or more solar panels;

wherein the one or more portable sensors are used to determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from a second coated area of the one or more solar panels equal to or greater than 1 $cm^2$ comprising non-uniformities in the at least one or more solar panels' cover glass, non-uniformities in a photovoltaic cell surface, and non-uniformities in the coating on the one or more solar panels;

wherein the signal processing circuit determines if the coating is too thick by determining if the light received from the second coated area of the one or more solar panels is shifted toward the reddish end of the light spectrum relative to the light received from the first coated area of the one or more solar panels by comparing the light reflection intensity in at least part of the red or infrared range of the light spectrum or the light reflection intensity in at least part of the ultraviolet range from the second coated area with the light reflection intensity in at least part of the red or infrared range of the light spectrum or the light reflection intensity in at least part of the ultraviolet range from the first coated area or comparing the light reflection intensity across the spectrum from both the first coated area and the second coated area to the expected spectrum reflection such as the reflected spectrum from a ¼ wave-thick index matching film;

wherein the signal processing circuit triggers a reduction in the speed of the rolling movement that moves the coating heads across the solar panel if the light received from the second coated area of the solar panel is shifted toward the reddish end of the light spectrum relative to the light received from the first coated area of the solar panel;

and wherein the closed loop feedback system monitors the one or more light sources with one or more portable sensors to detect if the one or more light sources drift during the process of determining if the light received from the second coated area of the one or more solar panels is shifted toward the reddish end of the light spectrum relative to the light received from the first coated area of the one or more solar panels.

18. The system of claim 17, wherein the signal processing circuit is further adapted to extract photometric data from said captured sensor signal and correlate the photometric data to one or more characteristics of the performance enhancement coating deposited by the mobile coating apparatus on said solar panel surface.

19. A method of increasing the performance of one or more solar panels in an outdoor solar panel array, comprising the following steps:
  A. retrofitting the one or more solar panels with an anti-reflective coating deposited by one or more coating heads that are moved across at least one or more solar panels by rolling motion;
  B. shining a light from one or more light sources onto a first coated area of the at least one or more solar panels equal to or greater than 1 cm² comprising non-uniformities in the at least one or more solar panels' cover glass, non-uniformities in a photovoltaic cell surface, and non-uniformities in the coating on the one or more solar panels;
  C. using one or more photodetectors and a signal processing circuit, determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from the first coated area of the one or more solar panels;
  D. shining a light from one or more light sources onto a second coated area of the at least one or more solar panels equal to or greater than 1 cm² comprising non-uniformities in the at least one or more solar panels' cover glass, non-uniformities in a photovoltaic cell surface, and non-uniformities in the coating on the one or more solar panels;
  E. using one or more photodetectors and a signal processing circuit, determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from the second uncoated area of the one or more solar panels;
  F. using a signal processing circuit to determine if the coating is too thick by determining if the light received from the second coated area of the one or more solar panels is shifted toward the reddish end of the light spectrum relative to the light received from the first coated area of the one or more solar panels by comparing the light reflection intensity in at least part of the red or infrared range of the light spectrum or the light reflection intensity in at least part of the ultraviolet range from the second coated area with the light reflection intensity in at least part of the red or infrared range of the light spectrum or the light reflection intensity in at least part of the ultraviolet range from the first coated area or comparing the light reflection intensity across the spectrum from both the first coated area and the second coated area to the expected spectrum reflection such as the reflected spectrum from a ¼ wave-thick index matching film;
  G. using the signal processing circuit to trigger a reduction in the speed of the rolling movement that moves the coating heads across the solar panel if the light received from the second coated area of the solar panel is shifted toward the reddish end of the light spectrum relative to the light received from the first coated area of the solar panel;
  H. and monitoring the one or more light sources with one or more photometric sensors to detect if the one or more light sources drift during the process of determining if the light received from the second coated area of the one or more solar panels is shifted toward the reddish end of the light spectrum relative to the light received from the first coated area of the one or more solar panels.

20. The method of claim 19, wherein the step of adjusting the means for controlling said solar panel coating apparatus comprises reading, by a human operator, data displayed on a display device to said human operator, wherein the human operator manually adjusts control parameters of the means for controlling said solar panel surface coating apparatus according to the data displayed.

21. The method of claim 19, wherein the step of adjusting the means for controlling said solar panel surface coating apparatus comprises a closed loop control system comprising a microprocessor that determines the adjustments based on analysis of photometric data.

22. The method of claim 19, wherein the step of adjusting the means for controlling said solar panel surface coating device comprises making adjustments to the rate of deposition of coating solution from the solar panel surface coating apparatus for optimizing the performance-enhancement properties of the coating.

23. The method of claim 19, wherein said photometric data are spectrally resolved intensity measurement data over a range of wavelengths.

24. The method of claim 19, wherein said photometric data are percent reflectance measurement data.

25. The method of claim 19, wherein said performance enhancement coating is an antireflection coating.

26. A method of increasing the performance of one or more solar panels in an outdoor solar panel array by applying a performance enhancing coating, comprising the following steps:

A. shining a light from one or more light sources onto a first area of the at least one or more solar panels equal to or greater than 1 cm² comprising non-uniformities in the one or more solar panels' cover glass and non-uniformities in a photovoltaic cell surface;

B. using one or more photodetectors and a signal processing circuit, determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from the first area of the one or more solar panels;

C. shining a light from one or more light sources onto a second area of the at least one or more solar panels equal to or greater than 1 cm² comprising non-uniformities in the solar panels' cover glass and non-uniformities in a photovoltaic cell surface;

D. using one or more photodetectors and a signal processing circuit, determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from the second area of the one or more solar panels;

E. retrofitting the one or more solar panels with a performance enhancing coating deposited by one or more coating heads that are moved across the one or more solar panels by rolling motion so that both the first and second areas are coated;

F. shining a light from one or more light sources onto the first area of the at least one or more solar panels equal to or greater than 1 cm² comprising non-uniformities in the one or more solar panels' cover glass, non-uniformities in a photovoltaic cell surface, and non-uniformities in the coating on the one or more solar panels;

G. using one or more photodetectors and a signal processing circuit, determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from the first area of the one or more solar panels;

H. shining a light from one or more light sources onto the second area of the at least one or more solar panels equal to or greater than 1 cm² comprising non-uniformities in the solar panels' cover glass, non-uniformities in a photovoltaic cell surface, and non-uniformities in the coating on the one or more solar panels;

I. using one or more photodetectors and a signal processing circuit, determine the light reflection intensity in at least part of the red or infrared range of the light spectrum using a bandpass filter or cutoff filter or the light reflection intensity in at least part of the ultraviolet, red, or infrared range by integrating the light received in at least one of these ranges from the second area of the one or more solar panels;

J. using a signal processing circuit, subtract the light reflection intensity determined in step G from the light reflection intensity determined in step B to determine the post-coating light reflection intensity difference for the first area;

K. using the signal processing circuit, subtract the light reflection intensity determined in step I from the light reflection intensity determined in step D to determine the post-coating light reflection intensity difference for the second area;

L. using the signal processing circuit, determine if the coating is too thick by determining if the post-coating light reflection intensity difference for the second area is shifted toward the reddish end of the light spectrum relative to the post-coating light reflection intensity difference for the first area by comparing the post-coating light reflection intensity differences from both the first area and the second area to the expected spectrum reflection such as the reflected spectrum from a ¼ wave-thick index matching film;

M. using the signal processing circuit to trigger a reduction in the speed of the rolling movement that moves the coating heads across the solar panel if the post-coating light reflection intensity difference for the second area is shifted toward the reddish end of the light spectrum relative to the post-coating light reflection intensity difference for the first area;

N. and monitoring the one or more light sources with one or more photometric sensors to detect if the one or more light sources drift during the process of determining if the post-coating light reflection intensity difference for the second area is shifted toward the reddish end of the light spectrum relative to the post-coating light reflection intensity difference for the first area.

27. The method of claim 26 wherein the performance enhancing coating is an antireflection coating.

* * * * *